United States Patent [19]

McDonnell et al.

[11] Patent Number: 6,033,873
[45] Date of Patent: Mar. 7, 2000

[54] DRUG BINDING PROTEIN

[75] Inventors: Peter Colon McDonnell, Elkins Park, Pa.; Peter Ronald Young, Lawrenceville, N.J.

[73] Assignee: Smithkline Beecham Corporation, Philadelphia, Pa.

[21] Appl. No.: 09/189,602

[22] Filed: Nov. 10, 1998

Related U.S. Application Data

[60] Division of application No. 08/746,788, Nov. 15, 1996, Pat. No. 5,869,043, which is a continuation-in-part of application No. 08/468,902, Jun. 6, 1995, abandoned, which is a continuation-in-part of application No. 08/469,421, which is a continuation-in-part of application No. PCT/US94/10529, Sep. 16, 1994, Pat. No. 5,777,097, and a continuation-in-part of application No. 08/250,975, May 31, 1994, Pat. No. 5,783,664, which is a continuation-in-part of application No. 08/123,175, Sep. 17, 1993, abandoned.

[51] Int. Cl.$^7$ .................................................. C12P 21/04
[52] U.S. Cl. ....................... 435/69.1; 536/23.2; 435/70.1; 435/252.1; 435/320.1; 435/325; 530/352
[58] Field of Search .................................. 536/23.1, 23.2, 536/23.5, 243; 435/320.1, 325, 252.1, 69.1, 70.1; 530/352

[56] References Cited

U.S. PATENT DOCUMENTS 5,663,313  9/1997  Hawkins et al. ........................ 536/23.1

FOREIGN PATENT DOCUMENTS

WO 97/02347  1/1997  WIPO .

OTHER PUBLICATIONS

Alberts et al., Molecular Biology of the Cell. 2$^{nd}$ Ed. Garland Publishing, Inc. N.Y. & London pp. 260–262, 1989.
Arai, K. et al., "Cytokines: Coordinators of Immune and Inflammatory Responses", *Annu. Rev. Biochem.*, 59: 783–836, 1990.
Lee, J.C. et al., "Inhibition of Monocyte Il–1 Production by the Anti–Inflammatory Compound, SK&F 86002", *Int. J. Immunopharmac.*, 10(7): 835–843, 1988.
Lee, J.C. et al., "Effect of SK & F86002 on cytokine production by human monocytes", *Agents and Actions*, 27:3–4, 1989.
Lee, J.C. et al., "Inhibition of Human Monocyte IL–1 Production by SK&F 86002", *Int. J. Immunotherapy* VI(1): 1–12, 1990.
Lee, J.C. et al., "A protein kinase involved in the regulation of inflammatory cytokine biosynthesis", *Nature*, 372:22–29, Dec. 1994.
McLaughlin M.M., et al., "Identification of Mitogen–activated Protein (MAP) Kinase–activated Protein Kinase–3, a Novel Substrate of CSBP p38 MAP Kinase", *J. Biol. Chem.* 271(14): 8488–8492, 1996.
Kumar, S. et al., "Human Mitogen–activated Protein Kinase CSBP1, but Not CSBP2, Complements a hog 1 Deletion in Yeast", *J. Biol. Chem.*, 270(49): 29043–29046, 1995.

Gaber, R.F. et al., "The Yeast Gene ERG6 Is Required for Normal Membrane Function but Is Not Essential for Biosynthesis for the Cell–Cycle–Sparking Sterol", *Molec. and Cellular Biol.*, (9)8: 3447–3456, 1989.
Marshall, C.J., "MAP kinase kinase kinase, MAP kinase kinase and MAP kinase", Current Opinion, *Genetics and Development*, 4: 82–89, 1994.
Cano, E. et al., "Parallel signal processing among mammalian MAPKs", *Elsevier Science Ltd.*, TIBS 20: 117–122, 1995.
Zervos, A.S. et al., "Mxi2, a mitogen–activated protein kinase that recognizes and phosphorylates Max protein", *Proc. Natl. Acad. Sci.*, 92: 10531–10534, 1995.
Jiang, Y. et al., "Characterization of the Structure and Function of a New Mitogen–activated Protein Kinase (p38β)", *J. Biol. Chem.*, 271(30): 17920–17926, 1996.
Lechner, C. et al., "ERK6, a mitogen–activated protein kinase involved in C2C12 myoblast differentiation", *Cell Biology*, 93: 4355–4359, 1996.
Mullis, K. et al. "Specific synthesis of DNA in vitro via a polymerase–catalyzed chain reaction", *Methods in Enzymol.*, 155(21): 335–350, 1987.
McHale, M.M. et al., "Expression of Human Recombinant cAMP Phosphodieterase Isozymes IV Reverses Grwoth Arrest Phenotypes in Phosphodiesterase–Deficient Yeast", *Molec. Pharmacol.*, 39: 109–113, 1990.
Han, J. et al., "A MAP Kinase Targeted by Endotoxin and Hypersomolarity in Mammalian Cells", *Science*, 265: 808–811, 1994.
Freshney, N.W. et al., "Interleukin–1 Activates a Novel Protein Kinase Cascade That Results in the Phosphorylation of Hsp27", *Cell*, 78: 1039–1049, 1994.
Brewster, J.L. et al. "An Osmosensing Signal Transduction Pathway in Yeast", *Science*, 259: 1760–1763, 1993.
Rouse, J. et al., "A Novel Kinase Cascade Triggered by Stress and Heat Shock That Stimulates MAPKAP Kinase–2 and Phosphorylation of the Small Heat Shock Proteins", *Cell*, 78: 1027–1037, 1994.
Mertens, S. et al., "SAP kinase–3, a new member of the family of mammalian stress–activated protein kinases", *FEBS Letters*, 383: 273–276, 1996.
MPsrch amino acid sequence alignment search (Nov. 1997).

*Primary Examiner*—Christina Y. Chan
*Assistant Examiner*—Patrick J. Nolan
*Attorney, Agent, or Firm*—Elizabeth J. Hecht; Ratner & Prestia; William T. King

[57] ABSTRACT

This invention relates to drug binding proteins, to genes encoding same and to assays and methods for screening pharmaceuticals. More specifically, this invention relates to a Cytokine Suppressive Anti-Inflammatory Drug (CSAID) binding protein CSBPβ, to a gene encoding same and to assays and screens useful in the evaluation and characterization of drugs of this pharmacologic class.

11 Claims, 3 Drawing Sheets

```
GCACGAGCGCAGCCGCCACGCCGGGGCCGCCGAGATCGGGTGCCCGGGATGAGCCTCATC    60
                                                   M   S   L   I

CGGAAAAAGGGCTTCTACAAGCAGGAGCTCAACAAGACCGCCTGGGAGCTGCCCAAGACC   120
 R   K   K   G   F   Y   K   Q   E   L   N   K   T   A   W   E   L   P   K   T

TACGTCTCCCCGACGCACGTCGGCAGCGGGGCCTATGGCTCCTGGTGCTCGGCCATCGAC   180
 Y   V   S   P   T   H   V   G   S   G   A   Y   G   S   W   C   S   A   I   D

AAGCGGTCAGGGGAGAAGGTGGCCATCAAGAAGCTGAGCCGACCCTTTCAGTCCGAGATT   240
 K   R   S   G   E   K   V   A   I   K   K   L   S   R   P   F   Q   S   E   I

TTCGCCAAGCGCGCCTACCGGGAGCTGCTGCTGCTGAAGCACATGCAGCATGAGAACGTC   300
 F   A   K   R   A   Y   R   E   L   L   L   L   K   H   M   Q   H   E   N   V

ATTGGGCTCCTGGATGTTTTCACCCCAGCCTCCTCCCTGCGCAACTTCTATGACTTCTAC   360
 I   G   L   L   D   V   F   T   P   A   S   S   L   R   N   F   Y   D   F   Y

CTGGTGATGCCCTTCATGCAGACGGATCTGCAGAAGATCATGGGGATGGAGTTCAGTGAG   420
 L   V   M   P   F   M   Q   T   D   L   Q   K   I   M   G   M   E   F   S   E

GAGAAGATCCAGTACCTGGTGTATCAGATGCTCAAAGGCCTTAAGTACATCCACTCTGCT   480
 E   K   I   Q   Y   L   V   Y   Q   M   L   K   G   L   K   Y   I   H   S   A

GGGGTCGTGCACAGGGACCTGAAGCCAGGCAACCTGGCTGTGAATGAGGACTGTGAACTG   540
 G   V   V   H   R   D   L   K   P   G   N   L   A   V   N   E   D   C   E   L

AAGATTCTGGATTTTGGGCTGGCGCGACATGCAGACGCCGAGATGACTGGCTACGTGGTG   600
 K   I   L   D   F   G   L   A   R   H   A   D   A   E   M   T   G   Y   V   V

ACCCGCTGGTACCGAGCCCCCGAGGTGATCCTCAGCTGGATGCACTACAACCAGACAGTG   660
 T   R   W   Y   R   A   P   E   V   I   L   S   W   M   H   Y   N   Q   T   V

GACATCTGGTCTGTGGGCTGTATCATGGCAGAGATGCTGACAGGGAAAACTCTGTTCAAG   720
 D   I   W   S   V   G   C   I   M   A   E   M   L   T   G   K   T   L   F   K
```

FIG. 1A

```
GGGAAAGATTACCTGGACCAGCTGACCCAGATCCTGAAAGTGACCGGGGTGCCTGGCACG   780
 G   K   D   Y   L   D   Q   L   T   Q   I   L   K   V   T   G   V   P   G   T

GAGTTTGTGCAGAAGCTGAACGACAAAGCGGCCAAATCCTACATCCAGTCCCTGCCACAG   840
 E   F   V   Q   K   L   N   D   K   A   A   K   S   Y   I   Q   S   L   P   Q

ACCCCCAGGAAGGATTTCACTCAGCTGTTCCCACGGGCCAGCCCCCAGGCTGCGGACCTG   900
 T   P   R   K   D   F   T   Q   L   F   P   R   A   S   P   Q   A   A   D   L

CTGGAGAAGATGCTGGAGCTAGACGTGGACAAGCGCCTGACGGCCGCGCAGGCCCTCACC   960
 L   E   K   M   L   E   L   D   V   D   K   R   L   T   A   A   Q   A   L   T

CATCCCTTCTTTGAACCCTTCCGGGACCCTGAGGAAGAGACGGAGGCCCAGCAGCCGTTT   1020
 H   P   F   F   E   P   F   R   D   P   E   E   E   T   E   A   Q   Q   P   F

GATGATTCCTTAGAACACGAGAAACTCACAGTGGATGAATGGAAGCAGCACATCTACAAG   1080
 D   D   S   L   E   H   E   K   L   T   V   D   E   W   K   Q   H   I   Y   K

GAGATTGTGAACTTCAGCCCCATTGCCCGGAAGGACTCACGGCGCCGGAGTGGCATGAAG   1140
 E   I   V   N   F   S   P   I   A   R   K   D   S   R   R   R   S   G   M   K

CTGTAGGGACTCATCTTGCATGGCACCGCCGGCCAGACACTGCCCAAGGACCAGTATTTG   1200
 L   *

TCACTACCAAACTCAGCCCTTCTTGGAATACAGCCTTTCAAGCAGAGGACAGAAGGGTCC   1260

TTCTCCTTATGTGGGAAATGGGCCTAGTAGATGCAGAATTCAAAGATGTCGGTTGGGAGA   1320

AACTAGCTCTGATCCTAACAGGCCACGTTAAACTGCCCATCTGGAGAATCGCCTGCAGGT   1380

GGGGCCCTTTCCTTCCCGCCAGAGTGGGGCTGAGTGGGCGCTGAGCCAGGCCGGGGGCCT   1440

ATGGCAGTGATGCTGTGTTGGTTTCCTAGGGATGCTCTAACGAATTACCACAAACCTGGT   1500

GGATTGAAACAGCAGAACTTGATTCCCTTACAGTTCTGGAGGCTGGAAATYTGGGATGGA   1560

GGTGTTGGCAGGGCTGTGGTCCCTTTGAAGGCTCTGGGGAAGAATCCTTCCTTGGCTCTT   1620

TTTAGCTTGTGGCGGCAGTGGGCAGTCCGTGGCATTCCCCAGCTTATTGCTGCATCACTC   1680
```

FIG. 1B

```
CAGTCTCTGTCTCTTCTGTTCTCTCCTCTTTTAACAACAGTCATTGGATTTAGGGCCCAC   1740

CCTAATCCTGTGTGATYTTATYTTGATCCTTATTAATTAAACCTGCAAATACTCTAGTTC   1800

CAAATAAAGTCACATTCTCAGGTTCCAGGTGGACATGA   1838
```

FIG. 1C

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 1838 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
GCACGAGCGC AGCCGCCACG CCGGGGCCGC CGAGATCGGG TGCCCGGGAT GAGCCTCATC      60

CGGAAAAAGG GCTTCTACAA GCAGGAGCTC AACAAGACCG CCTGGGAGCT GCCCAAGACC     120

TACGTCTCCC CGACGCACGT CGGCAGCGGG GCCTATGGCT CCTGGTGCTC GGCCATCGAC     180

AAGCGGTCAG GGGAGAAGGT GGCCATCAAG AAGCTGAGCC GACCCTTTCA GTCCGAGATT     240

TTCGCCAAGC GCGCCTACCG GGAGCTGCTG CTGCTGAAGC ACATGCAGCA TGAGAACGTC     300

ATTGGGCTCC TGGATGTTTT CACCCCAGCC TCCTCCCTGC GCAACTTCTA TGACTTCTAC     360

CTGGTGATGC CCTTCATGCA GACGGATCTG CAGAAGATCA TGGGGATGGA GTTCAGTGAG     420

GAGAAGATCC AGTACCTGGT GTATCAGATG CTCAAAGGCC TTAAGTACAT CCACTCTGCT     480

GGGGTCGTGC ACAGGGACCT GAAGCCAGGC AACCTGGCTG TGAATGAGGA CTGTGAACTG     540

AAGATTCTGG ATTTTGGGCT GGCGCGACAT GCAGACGCCG AGATGACTGG CTACGTGGTG     600

ACCCGCTGGT ACCGAGCCCC CGAGGTGATC CTCAGCTGGA TGCACTACAA CCAGACAGTG     660

GACATCTGGT CTGTGGGCTG TATCATGGCA GAGATGCTGA CAGGGAAAAC TCTGTTCAAG     720

GGGAAAGATT ACCTGGACCA GCTGACCCAG ATCCTGAAAG TGACCGGGGT GCCTGGCACG     780

GAGTTTGTGC AGAAGCTGAA CGACAAAGCG GCCAAATCCT ACATCCAGTC CCTGCCACAG     840

ACCCCCAGGA AGGATTTCAC TCAGCTGTTC CCACGGGCCA GCCCCCAGGC TGCGGACCTG     900

CTGGAGAAGA TGCTGGAGCT AGACGTGGAC AAGCGCCTGA CGGCCGCGCA GGCCCTCACC     960

CATCCCTTCT TTGAACCCTT CCGGGACCCT GAGGAAGAGA CGGAGGCCCA GCAGCCGTTT    1020

GATGATTCCT TAGAACACGA GAAACTCACA GTGGATGAAT GGAAGCAGCA CATCTACAAG    1080

GAGATTGTGA ACTTCAGCCC CATTGCCCGG AAGGACTCAC GGCGCCGGAG TGGCATGAAG    1140

CTGTAGGGAC TCATCTTGCA TGGCACCGCC GGCCAGACAC TGCCCAAGGA CCAGTATTTG    1200

TCACTACCAA ACTCAGCCCT TCTTGGAATA CAGCCTTTCA AGCAGAGGAC AGAAGGGTCC    1260

TTCTCCTTAT GTGGGAAATG GGCCTAGTAG ATGCAGAATT CAAAGATGTC GGTTGGGAGA    1320

AACTAGCTCT GATCCTAACA GGCCACGTTA AACTGCCCAT CTGGAGAATC GCCTGCAGGT    1380

GGGGCCCTTT CCTTCCCGCC AGAGTGGGGC TGAGTGGGCG CTGAGCCAGG CCGGGGGCCT    1440

ATGGCAGTGA TGCTGTGTTG GTTTCCTAGG GATGCTCTAA CGAATTACCA CAAACCTGGT    1500
```

```
GGATTGAAAC AGCAGAACTT GATTCCCTTA CAGTTCTGGA GGCTGGAAAT YTGGGATGGA      1560

GGTGTTGGCA GGGCTGTGGT CCCTTTGAAG GCTCTGGGGA AGAATCCTTC CTTGGCTCTT      1620

TTTAGCTTGT GGCGGCAGTG GGCAGTCCGT GGCATTCCCC AGCTTATTGC TGCATCACTC      1680

CAGTCTCTGT CTCTTCTGTT CTCTCCTCTT TTAACAACAG TCATTGGATT TAGGGCCCAC      1740

CCTAATCCTG TGTGATYTTA TYTTGATCCT TATTAATTAA ACCTGCAAAT ACTCTAGTTC      1800

CAAATAAAGT CACATTCTCA GGTTCCAGGT GGACATGA                              1838
```

(2) INFORMATION FOR SEQ ID NO:2:

(i) SEQUENCE CHARACTERISTICS:
    (A) LENGTH: 365 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:2:

```
Met Ser Leu Ile Arg Lys Lys Gly Phe Tyr Lys Gln Glu Leu Asn Lys
 1               5                  10                  15

Thr Ala Trp Glu Leu Pro Lys Thr Tyr Val Ser Pro Thr His Val Gly
            20                  25                  30

Ser Gly Ala Tyr Gly Ser Trp Cys Ser Ala Ile Asp Lys Arg Ser Gly
        35                  40                  45

Glu Lys Val Ala Ile Lys Lys Leu Ser Arg Pro Phe Gln Ser Glu Ile
    50                  55                  60

Phe Ala Lys Arg Ala Tyr Arg Glu Leu Leu Leu Lys His Met Gln
65                  70                  75                  80

His Glu Asn Val Ile Gly Leu Leu Asp Val Phe Thr Pro Ala Ser Ser
                85                  90                  95

Leu Arg Asn Phe Tyr Asp Phe Tyr Leu Val Met Pro Phe Met Gln Thr
            100                 105                 110

Asp Leu Gln Lys Ile Met Gly Met Glu Phe Ser Glu Glu Lys Ile Gln
        115                 120                 125

Tyr Leu Val Tyr Gln Met Leu Lys Gly Leu Lys Tyr Ile His Ser Ala
    130                 135                 140

Gly Val Val His Arg Asp Leu Lys Pro Gly Asn Leu Ala Val Asn Glu
145                 150                 155                 160

Asp Cys Glu Leu Lys Ile Leu Asp Phe Gly Leu Ala Arg His Ala Asp
                165                 170                 175

Ala Glu Met Thr Gly Tyr Val Val Thr Arg Trp Tyr Arg Ala Pro Glu
            180                 185                 190

Val Ile Leu Ser Trp Met His Tyr Asn Gln Thr Val Asp Ile Trp Ser
        195                 200                 205

Val Gly Cys Ile Met Ala Glu Met Leu Thr Gly Lys Thr Leu Phe Lys
    210                 215                 220

Gly Lys Asp Tyr Leu Asp Gln Leu Thr Gln Ile Leu Lys Val Thr Gly
225                 230                 235                 240

Val Pro Gly Thr Glu Phe Val Gln Lys Leu Asn Asp Lys Ala Ala Lys
                245                 250                 255

Ser Tyr Ile Gln Ser Leu Pro Gln Thr Pro Arg Lys Asp Phe Thr Gln
            260                 265                 270

Leu Phe Pro Arg Ala Ser Pro Gln Ala Ala Asp Leu Leu Glu Lys Met
        275                 280                 285
```

```
Leu Glu Leu Asp Val Asp Lys Arg Leu Thr Ala Ala Gln Ala Leu Thr
    290                 295                 300

His Pro Phe Phe Glu Pro Phe Arg Asp Pro Glu Glu Glu Thr Glu Ala
305                 310                 315                 320

Gln Gln Pro Phe Asp Asp Ser Leu Glu His Glu Lys Leu Thr Val Asp
                325                 330                 335

Glu Trp Lys Gln His Ile Tyr Lys Glu Ile Val Asn Phe Ser Pro Ile
            340                 345                 350

Ala Arg Lys Asp Ser Arg Arg Arg Ser Gly Met Lys Leu
        355                 360                 365
```

(2) INFORMATION FOR SEQ ID NO:3:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
GATCCGGTAC CATGGATTAT AAAGATGATG ATGATAAAAG CCTCATCCGG AAAAAGGGCT      60

TCTACAAGCA GGAGCT                                                     76
```

(2) INFORMATION FOR SEQ ID NO:4:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
CCTGCTTGTA GAAGCCCTTT TTCCGGATGA GGCTTTTATC ATCATCATCT TTATAATCCA      60

TGGTACCG                                                              68
```

DRUG BINDING PROTEIN

CROSS-REFERENCE TO RELATED APPLICATIONS

This application is a divisional of U.S. application Ser. No. 08/746,788, filed on Nov. 15, 1996, now U.S. Pat. No. 5,869,043, which is a continuation-in-part of U.S. application Ser. No. 08/468,902, filed on Jun. 6, 1995, now abandoned, which is a continuation-in-part of U.S. application Ser. No. 08/469,421, filed on Jun. 6, 1995, now U.S. Pat. No. 5,777,097, which is a continuation-in-part of PCT/US94/10529, filed on Sep. 16, 1994. U.S. application Ser. No. 08/468,902, U.S. application Ser. No. 08/469,421, and PCT/US94/10529 are continuation-in-parts of U.S. application Ser. No. 08/250,975, filed on May 31, 1994, now U.S. Pat. No. 5,783,664, which is a continuation-in-part of U.S. application Ser. No. 08/123,175, filed on Sep. 17, 1993, now abandoned, the contents of all of which are incorporated herein by reference in their entireties.

FIELD OF THE INVENTION

This invention relates, inter alia, to drug binding proteins, to genes encoding same and to assays and methods for screening pharmaceuticals. More specifically, this invention relates to the Cytokine Suppressive Anti-Inflammatory Drug (CSAID) binding proteins CSBPβ, to genes encoding same and to assays and screens useful in the evaluation and characterization of drugs of this pharmacologic class.

BACKGROUND OF THE INVENTION

Cytokines play an important role in regulating the cellular response during inflammation and other immune functions. Of particular interest are the cytokines interleukin-1 (IL-1, α and β) and tumor necrosis factor (TNF, α and β), which are the intercellular proteins involved in the initial step of the inflammatory response cascade (Arai, et al., *Ann. Rev. Biochem.* 59: 783–836 (1990)). Thus, there has been a substantial amount of research recently devoted to interfering with the production of IL- 1 and TNF in response to an inflammatory stimulus.

One therapeutic approach involves suppressing the production of IL-1 and TNF at the level of transcription and/or translation and/or secretion. The activities associated with certain of pyridinyl imidazoles led to a class of compounds referred to as "CSAIDs", or Cytokine Suppressing Anti-Inflammatory Drugs. These compounds appear to arrest the expression of IL-1 and TNF predominantly at the translational level, although a lesser effect on transcription has also been observed but effects on other steps cannot be ruled out.

The pyridinyl imidazole, 5-(4-pyridyl)-6(4-fluorophenyl)-2,3-hydroimidazo(2,1-b)thiazole (SK&F 86002) was identified as the prototypic CSAID. The basis for its activity has been established and characterized (Lee, et al, *Int'l. J. Immunopharm.* 10(7): 835–843 (1988); *Agents and Actions* 27(3/4): 277–279 (1989) and *Int'l. J. Immunother.* 6(1):1–12 (1990)). SAR studies suggest that cytokine suppressive effect of the pyridinyl imidazoles represents a unique activity independent of their inhibitory effects on eicosanoid and leukotriene production.

Since the CSAIDs have substantial potential as novel anti-inflammatory therapeutic agents, there is significant interest in characterizing, their mechanism of action at the molecular level, as well as obtaining compounds with increased selectivity and potency. Specifically, identification and characterization of the CSAID molecular target would enhance the understanding of the biochemical processes involved in inflammation and aid in the design and screening of more potent anti-inflammatory drugs. This invention discloses, inter alia, the purification and characterization of additional CSAID binding proteins (CSBPs).

BRIEF DESCRIPTION OF THE INVENTION

The DNAs of this invention, such as the specific sequences disclosed herein, are useful in that they encode sequences disclosed herein, are useful in that they encode the genetic information required for the expression of the novel CSBPβs. Additionally, the sequences may be used as probes in order to isolate and identify any additional members of the CSBPβ family as well as forming the basis of antisense therapy for disease conditions which are characterized by atypical expression of the CSBPβ gene. The novel protein itself is useful directly as a therapeutic or diagnostic agent well as a component in a screening system for compounds which are antagonists or agonists of CSAID binding activity. The protein is also useful for eliciting antibody production in heterologous species, said antibodies being useful for the aforesaid diagnostic, therapeutic and screening applications. These and additional uses for the reagents described herein will become apparent to those of ordinary skill in the art upon reading this specification.

BRIEF DESCRIPTION OF THE FIGURES

FIGS. 1A, 1B and 1C illustrate (SEQ ID NOS: 1 and 2) the nucleic acid sequence and amino sequence of a CSBPβ.

DETAILED DESCRIPTION OF THE INVENTION

Using the information provided herein, such as the polynucleotide sequence set out in FIGS. 1A, 1B and 1C (SEQ ID NO: 1) a polynucleotide of the present invention encoding CSBPβ may be obtained using standard cloning and screening procedures, such as those for cloning cDNAs using mRNA from testis and T cells as starting material. Illustrative of the invention, a partial fragment of the polynucleotide set out in FIGS 1A, 1B and 1C was discovered in a cDNA library derived from cells of human testis using the expressed sequence tag (EST) analysis (Adams, M. D., et al. *Science,* (1991), 252:1651–1656; Adams, M. D. et al., *Nature,* (1992), 355:632–634; Adams, M. D., et al., *Nature,* (1995), 377 Supp:3–174). A longer cDNA corresponding to the sequence in FIGS. 1A, 1B and 1C and containing a complete open reading frame for protein tranlsation as indicated was subsequently cloned via hybridization using standard cloning and screening procedures from an activated T cell library.

CSBPβ of the invention is structurally related to other proteins of the CSBP family. The nucleotide sequence encoding the CSBPβ of this invention has about 58–73% identity over its entirety with other human members of the MAP Kinase family.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

The coding sequence which encodes the polypeptide may be identical to the coding sequence of the polynucleotide shown in FIGS. 1A, 1B and 1C (SEQ ID NO: 1). It also may be a polynucleotide with a different sequence, which, as a result of the redundancy (degeneracy) of the genetic code, also encodes the polypeptide of FIGS. 1A, 1B and 1C (SEQ ID NO: 2).

Polynucleotides of the present invention which encode the polypeptide of FIGS. 1A, 1B and 1C (SEQ ID NO: 2) may include, but are not limited to, the coding sequence for the mature polypeptide, by itself; the coding sequence for the mature polypeptide and additional coding sequences, such as those encoding a leader or secretory sequence, such as a pre-, or pro- or prepro- protein sequence; and the coding sequence of the mature polypeptide, with or without the aforementioned additional coding sequences, together with additional non-coding sequences, including, but not limited to, introns and non-coding 5' and 3' sequences, such as the transcribed, non-translated sequences that play a role in transcription, and mRNA processing, including splicing and polyadenylation signals, for example, for ribosome binding and stability of mRNA. Coding sequences which provide additional functionalities may also be incorporated into the polypeptide. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in the pQE vector (Qiagen, Inc.). As described in Gentz et al., *Proc. Natl. Acad. Sci., USA,* 1989, 86:821–824, for instance, hexa-histidine provides for convenient purification of the fusion protein. In other embodiments the marker sequence is a HA tag. The HA tag corresponds to an epitope derived of influenza hemagglutinin protein, which has been described by Wilson et al., *Cell,* 1984, 37:767, for instance. Many other such tags are commercially abatable.

In accordance with the foregoing, the term "polynucleotide encoding a polypeptide" as used herein also encompasses polynucleotides that include a single continuous region or discontinuous regions encoding the polypeptide (for example, interrupted by introns) together with additional regions, that also may contain coding and/or non-coding sequences.

The present invention further relates to variants of the polynucleotides which encode for fragments, analogs and derivatives of the polypeptide having the deduced amino acid sequence of FIGS. 1A, 1B and 1C (SEQ ID NO: 2). A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequence CSBPβ set out in FIGS. 1A, 1B and 1C (SEQ ID NO: 2); variants, analogs, derivatives and fragments thereof, and fragments of the variants, analogs and derivatives.

Further particularly preferred are polynucleotides encoding CSBPβ variants, analogs, derivatives and fragments, and variants, analogs and derivatives of the fragments, which have the amino acid sequence of the CSBPβ polypeptide of FIGS. 1A, 1B and 1C (SEQ ID NO: 2) in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the CSBPβ. Also especially preferred in this regard are conservative substitutions. Most highly preferred are polynucleotides encoding polypeptides having the amino acid sequence of FIGS. 1A, 1B and 1C (SEQ ID NO: 2), without substitutions.

Further preferred embodiments of the invention are polynucleotides that are at least 75% identical to a polynucleotide encoding the CSBPβ polypeptide having the amino acid sequence set out in FIGS. 1A, 1B and 1C (SEQ ID NO: 2), and polynucleotides which are complementary to such polynucleotides. Most highly preferred are polynucleotides that comprise a region that is at least 80% identical to a polynucleotide encoding the CSBPβ polypeptide of the human cDNA of the deposited clone and polynucleotides complementary thereto. In this regard, polynucleotides at least 90% identical to the same are particularly preferred, and those with at least 95% are especially preferred. Furthermore, those with at least 97% are highly preferred and those with at least 98–99% are most highly preferred, with at least 99% being the most preferred.

Particularly preferred embodiments in this respect, moreover, are polynucleotides which encode polypeptides which retain substantially the same biological function or activity as the mature polypeptide encoded by the cDNA of FIGS. 1A, 1B and 1C (SEQ ID NO: 2).

The present invention further relates to polynucleotides that hybridize to the polynucleotide encoding a polypeptide of this invention. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

The polynucleotides of this invention may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may facilitate protein trafficking, may prolong or shorten protein half-life or may facilitate manipulation of a protein for assay or production, among other things. As generally is the case in situ, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Polypeptides

The present invention further relates to a CSBPβ polypeptide which has the deduced amino acid sequence of FIGS. 1A, 1B and 1C SEQ ID NO: 2.

The invention also relates to fragments, analogs and derivatives of these polypeptides. The terms "fragment," "derivative" and "analog" when referring to the polypeptide of FIGS. 1A, 1B and 1C (SEQ ID NO: 2), mean a polypeptide which retains essentially the same biological function or activity as such polypeptide, i.e. functions as a CSBPβ, or retains the ability to bind the ligand or the binding molecules even though the polypeptide does not otherwise function as a CSBPβ. Thus, an analog includes, for example, a proprotein which can be activated by cleavage of the proprotein portion to produce an active mature polypeptide.

The polypeptide of the present invention may be a recombinant polypeptide, a natural polypeptide or a synthetic polypeptide. In certain preferred embodiments, it is a recombinant polypeptide.

The fragment, derivative or analog of the polypeptide of FIGS. 1A, 1B and 1C (SEQ ID NO: 2) may be (i) one in which one or more of the amino acid residues are substituted with a conserved or non-conserved amino acid residue (preferably a conserved amino acid residue) and such substituted amino acid residue may or may not be one encoded by the genetic code; (ii) one in which one or more of the amino acid residues includes a substituent group; (iii) one in which the mature polypeptide is fused with another compound, such as a compound to increase the half-life of the polypeptide (for example, polyethylene glycol); or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Among the particularly preferred embodiments of the invention in this regard are polypeptides having the amino acid sequence of CSBPβ set out in FIGS. 1A, 1B and 1C (SEQ ID NO: 2), variants, analogs, derivatives and fragments thereof, and variants, analogs and derivatives of the fragments. Further particularly preferred embodiments of the invention in this regard are polypeptides having the amino acid sequence of CSBPβ, variants, analogs, derivatives and fragments thereof, and variants, analogs and derivatives of the fragments which retain the CSAID binding activity/function of CSBPβ.

Further particularly preferred in this regard are variants, analogs, derivatives and fragments, and variants, analogs and derivatives of the fragments, having the amino acid sequence of the CSBPβ polypeptide of FIGS. 1A, 1B and 1C (SEQ ID NO: 2), in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the CSBPβ. Also especially preferred in this regard are conservative substitutions. Most highly preferred are polypeptides having the amino acid sequence of FIGS. 1A, 1B and 1C (SEQ ID NO: 2) without substitutions.

The polypeptides and polynucleotides of the present invention are preferably provided in an isolated form, and preferably are purified to homogeneity.

The polypeptides of the present invention include the polypeptide of SEQ ID NO: 2 (in particular the mature polypeptide) as well as polypeptides which have at least 80% identity to the polypeptide of SEQ ID NO: 2 and more preferably at least 90% similarity (more preferably at least 90% identity) to the polypeptide of SEQ ID NO: 2 and still more preferably at least 95% similarity (still more preferably at least 95% identity) to the polypeptide of SEQ ID NO: 2 and also include portions of such polypeptides with such portion of the polypeptide generally containing at least 30 amino acids and more preferably at least 50 amino acids.

Polypeptide Fragments

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention. Fragments may be "free standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a CSBPβ polypeptide of the present comprised within a precursor polypeptide designed for expression in a host and having heterologous pre and pro-polypeptide regions fused to the amino terminus of the CSBPβ fragment and an additional region fused to the carboxyl terminus of the fragment. Therefore, fragments in one aspect of the meaning intended herein, refers to the portion or portions of a fusion polypeptide or fusion protein derived CSBPβ.

As representative examples of polypeptide fragments of the invention, there may be mentioned those which have from about 5–15, 10–20, 15–40, 30–55, 41–75, 41–80, 41–90, 50–100, 75–100, 90–115, 100–125, and 110–113 amino acids in length.

In this context "about" includes the particularly recited range and ranges larger or smaller by several, a few, 5, 4, 3, 2 or 1 amino acid residues at either extreme or at both extremes. For instance, about 40–90 amino acids in this context means a polypeptide fragment of 40 plus or minus several, a few, 5, 4, 3, 2 or 1 amino acid residues to 90 plus or minus several a few, 5, 4, 3, 2 or 1 amino acid residues, i.e., ranges as broad as 40 minus several amino acids to 90 plus several amino acids to as narrow as 40 plus several amino acids to 90 minus several amino acids. Highly preferred in this regard are the recited ranges plus or minus as many as 5 amino acids at either or at both extremes. Particularly highly preferred are the recited ranges plus or minus as many as 3 amino acids at either or at both the recited extremes. Especially particularly highly preferred are ranges plus or minus 1 amino acid at either or at both extremes or the recited ranges with no additions or deletions. Most highly preferred of all in this regard are fragments from about 5–15, 10–20, 15–40, 30–55, 41–75, 41–80, 41–90, 50–100, 75–100, 90–115, 100–125, and 110–113 amino acids long.

Among especially preferred fragments of the invention are truncation mutants of CSBPβ. Truncation mutants include CSBPβ polypeptides having the amino acid sequence of FIGS. 1A, 1B and 1C (SEQ D NO: 2), or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Particularly preferred fragments of the membrane bound receptors of this invention, include soluble forms of the receptor comprising the extracellular domain without its attendant transmembrane and cytoplasmic domain or transmenbrane region deletions resulting a receptor in which the extracellular domain is fused directly to the cytoplasmic domain. See for example, published PCT application number WO94/03620. Fragments having the size ranges set out above also are preferred embodiments of truncation fragments, which are especially preferred among fragments generally.

Also preferred in this aspect of the invention are fragments characterized by structural or functional attributes of CSBPβ. Preferred embodiments of the invention in this regard include fragments that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of CSBPβ.

Among highly preferred fragments in this regard are those that comprise regions of CSBPβ that combine several structural features, such as several of the features set out above. In this regard, the regions defined by the residues about 10 to about 20, about 40 to about 50, about 70 to about 90 and about 100 to about 113 of FIGS. 1A, 1B and 1C, which all are characterized by amino acid compositions highly characteristic of turn-regions, hydrophilic regions, flexible-regions, surface-forming regions, and high antigenic index-regions, are especially highly preferred regions. Such regions may be comprised within a larger polypeptide or may be by themselves a preferred fragment of the present invention, as discussed above. It will be appreciated that the term "about" as used in this paragraph has the meaning set out above regarding fragments in general.

Further preferred regions are those that mediate activities of CSBPβ. Most highly preferred in this regard are fragments that have a chemical, biological or other activity of CSBPβ, including those with a similar activity or an improved activity, or with a decreased undesirable activity. Highly preferred in this regard are fragments that contain regions that are homologs in sequence, or in position, or in both sequence and to active regions of related polypeptides.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspond to the preferred fragments, as discussed above.

Vectors, Host Cells and Expression

The proteins of this invention are preferably made by recombinant genetic engineering techniques. The isolated nucleic acids, particularly the DNAs, can be introduced into expression vectors by operatively linking the DNA to the necessary expression control regions (e.g. regulatory regions) required for gene expression. The vectors can be introduced into the appropriate host cells such as prokaryotic (e.g., bacterial), or eukaryotic (e.g., yeast or mammalian) cells by methods well known in the art (Ausubel et al., supra). The coding sequences for the desired proteins having been prepared or isolated, can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage α (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coil* and *Bacillus subtilis*), pBD9 (Bacillus), pIJ61 (Streptomyces), pUC6 (Streptomyces), YIp5 (Saccharomyces), a baculovirus insect cell system, , YCp19 (Saccharomyces). See, generally, "DNA Cloning": Vols. I & II, Glover et al., eds. IRL Press Oxford (1985) (1987) and; T. Maniatis et al. "Molecular Cloning", Cold Spring Harbor Laboratory (1982).

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. The subunit antigens of the present invention can be expressed using, for example, the *E. coli* tac promoter or the protein A gene (spa) promoter and signal sequence. Leader sequences can be removed by the bacterial host in post-translational processing. See, L., U.S. Pat. Nos. 4,431,739; 4,425,437; 4,338,397.

In addition to control sequences, it may be desirable to add regulatory sequences which allow for regulation of the expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the particular protein of interest may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases, it may be desirable to add sequences which cause the secretion of the polypeptide from the host organism, with subsequent cleavage of the secretory signal. Alternatively, gene fusions may be created whereby the gene encoding the binding protein of interested is fused to a gene encoding a product with other desirable properties. For example, a fusion partner could provide known assayable activity (e.g., enzymatic) which could be used as an alternative means of selecting the binding protein. The fusion partner could be a structural element, such as a cell surface element such that the binding protein (a normally cytosolic component) could be displayed on the cell surface in the form of a fusion protein. Alternatively, it could be peptide or protein fragment which can be detected with specific antibodies and reagents, and may act as an aid to purification (eg His tail, Glutathione S-transferase fusion). It may also be desirable to produce mutants or analogs of the protein of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis and the formation of fusion proteins, are well known to those skilled in the art. See, e.g., T. Maniatis et al., supra; *DNA Cloning,* Vols. I and II, supra; *Nucleic Acid Hybridization,* supra.

A number of prokaryotic expression vectors are known in the art. See, e.g., U.S. Pat. Nos. 4,578,355; 4,440,859; 4,436,815; 4,431,740; 4,431,739; 4,428,941; 4,425,437; 4,418,149; 4,411,994; 4,366,246; 4,342,832; see also U.K. Patent Applications GB 2,121,054; GB 2,008,123; GB 2,007,675; and European Patent Application 103,395. Yeast expression vectors are also known in the art. See, e.g., U.S. Pat. Nos. 4,446,235; 4,443,539; 4,430,428; see also European Patent Applications 103,409; 100,561; 96,491. pSV2neo (as described in *J. Mol. Appl. Genet.* 1:327–341) which uses the SV40 late promoter to drive expression in mammalian cells or pCDNA1neo, a vector derived from pCDNA1(*Mol. Cell Biol.* 7:4125–29) which uses the CMV promoter to drive expression. Both these latter two vectors can be employed for transient or stable(e.g. using G418 or hygromycin resistance) expression in mammalian cells. Insect cell expression systems, e.g., Drosophila, are also useful, see for example, PCT applications U.S. Ser. No. 89/05155 and U.S. Ser. No. 91/06838 as well as EP application 88/304093.3 and Baculovirus expression systems.

Depending on the expression system and host selected, the proteins of the present invention are produced by growing host cells transformed by an expression vector described above under conditions whereby the protein of interest is expressed. The protein is then isolated from the host cells and purified. If the expression system secretes the protein into growth media, the protein can be purified directly from the media If the protein is not secreted, it is isolated from cell lysates or recovered from the cell membrane fraction. The selection of the appropriate growth conditions and recovery methods are within the skill of the art.

An alternative method to identify proteins of the present invention is by constructing gene libraries, using the resulting clones to transform *E. coli* and pooling and screening individual colonies using polyclonal serum or monoclonal antibodies to the desired binding protein.

The proteins of the present invention may also be produced by chemical synthesis such as solid phase peptide synthesis, using known amino acid sequences or amino acid sequences derived from the DNA sequence of the genes of interest. Such methods are known to those skilled in the art. Chemical synthesis of peptides is not particularly preferred. assays This invention also provides a method for determining whether a ligand previously not known to bind to a CSBPβ can bind to such a protein. The method comprises contacting the ligand to be identified with cytosolic fraction from mammalian cells and measuring its ability to compete with a known radioactive CSAID, in a CSAIDs binding assay (Lee et. al Nature 372:739–746; and previous CSBP filings). Alternative methods include contacting the ligand to be identified with a whole-cell expressing the coding sequence of a CSBPβ under conditions sufficient for binding of ligands previously identified as binding to such a receptor. In other embodiments cell membrane or cytosolic fractions comprising CSBPβ fusions or isolated CSBPβ free or immobilized on solid supports may be used to measure binding of the ligand to be tested. When recombinant cells are used for purposes of expression of the CSBPβ it is preferred to use cells with little or no endogenous CSBPβ activity so that binding if any is due to the presence of the expressed protein of interest. Alternatively, the CSBPβ is engineered as a fusion to a peptide or protein fragment allowing separation from endogenous cellular proteins which might contribute to binding. As mentioned previously, a specifically designed indicator of receptor binding can be constructed. For example a fusion protein can be made by fusing the CSBPβ of this invention with a protein domain which is sensitive to CSBPβ/ligand binding. Such a domain referred to here as an indicator domain is capable, itself, or in association with accessory molecules, of generating an analytically detectable signal which is indicative of receptor ligand binding. A variation of this approach is to express CSBPβ as a fusion protein (e.g., fused to FLAG peptide) in THP.1 or other mammalian cells, and to use the fusion peptide as a means of isolating the recombinant CSBPβ after suitable stimulation and pretreatment of THP.1 cells. Such expression can be achieved with numerous mammalian expression vectors which utilize viral promoters, eg CMV, RSV and polyadenylation sequences, et. SV40, bovine growth hormone, and a selectable marker such as G418 or hygromycin for selection of stable transfectants.

Cytosolic preparations from transfected or transformed cells expressing such fusions may be employed. All of the above techniques that are useful for ligand identification are also useful in drug screening and drug development protocols.

Alternatively, the purified recombinant protein could be used to substitute for crude THP.1 cell lysates in a competitive binding assay with SB 202190 or a related compound (Lee et al., Nature 372:739–746) . This assay is useful to screen for novel compound which bind CSBPβ, or as a way to assess alterations to compound which is known to bind. The availability of purified protein allows alternative configurations of the assay from those described previously for the crude material. For example, if the protein is covalently linked to a tag, such a protein binding site for configuration in a colorimetic assay, e.g., conjugated antibody, or to an enzyme for direct detection of enzyme activity, e.g., horseradish peroxidase or alkaline phosphatase, binding to novel compounds displayed on a solid matrix could be detected. Such compounds could include low molecular weight organic molecules, peptides, peptoids, and proteins. In the latter case, the protein can be used as a way to isolate other proteins in its signaling cascade, for example, those that are in the pathway for activation of cytokine translation in activated monocytes. The protein may also be used to isolate naturally occurring regulatory molecules within mammalian cells that act by a CSAIDs binding mechanism. Finally, the protein can be used to identify target peptides displayed on the surface of phage.

The knowledge that the CSBPβ encodes protein kinases suggests that recombinant forms can be used to establish a protein kinase activity. Typically this would involve the direct incubation of CSBPβ with a protein or peptide substrate in the presence of $\gamma$-$^{32}$P-ATP, followed by the measurement of radioactivity incorporated into the substrate by separation and counting. Separation methods include immunoprecipitation, conjugation of substrate to a bead allowing separation by centrifugation or determination of incorporation by scintillation proximity assay, SDS-PAGE followed by autoradiography or biosensor analysis. While the specific substrates are not yet known, candidates include CSBPβ itself (autophosphorylation), myelin basic protein, ATF2, MAPKAP kinase-2, MAPKAP kinase-3 (see McLaughlin et al., (1996) J. Biol. Chem. 271:8488–8492 and references therein) and peptides related to known MAP kinase substrates. Other substances might be discovered by incubating CSBPβ with random peptides conjugated to solid supports or displayed by phage (see above) or by incubation of CSBPβ with mammalian cell lysates (e.g. THP.1 cell lysates) and $\gamma$-$^{32}$P- ATP, followed by separation of the labelled target proteins, and sequencing. Kinase activity may also be detected by use of antiphosphotyrosine antibodies. The protein kinase activity of CSBPβ may require incubation with a specific MAP kinase kinase. This may be achieved by preincubating CSBPβ with lysates from stimulated eukaryotic cells (e.g., LPS treated THP.1 cells) and ATP. Alternatively, it may be possible to isolate a more active form of CSBPβ from HOG1 deletion strains of yeast expressing the human CSBPβ and grown in high osmolarity conditions (see for example Kumar et al., (1995) J. Biol. Chem. 270:29043–29046).

These assays permit the discovery and modification of compounds which inhibit CSBPβ kinase activity in vitro, a known property of CSAIDS (Lee, et al., *Nature*, supra). Such compounds will block cytokine synthesis in a comparable fashion to the compounds described herein. They could also lead to the discovery of novel substrates which themselves may be viable targets for discovery of novel compounds which block cytokine production.

It is expected that CSBPβs, like other MAP kinases, will be activated by a MAP kinase kinase , hence the recombinant protein would allow the establishment of a second assay which measures the ability of CSBPβ to be phosphorylated by putative MAP kinase kinases. In this case fractions from stimulated cell lysates (eg THP.1 cells stimulated with LPS) are incubated with CSBPβ in the presence of $\gamma$-$^{32}$P-ATP, and the incorporation of $^{32}$P-label into CSBPβ measured by separation and counting. Separation can be achieved in a number of ways: one way is to use a CSBPβ fused to a peptide or protein and separate via affinity chromatography or immunoprecipitation with the peptide or protein directed antibody. Alternatively, the CSBPβ can be directly conjugated to beads or bound through a fusion peptide or protein (e.g., FLAG (peptide), glutathionine-S-transferase) and separated by centrifugation after incubation with cell lysates. Also tyrosine phosphorylation of CSBPβ could be detected by immunoprecipitation or immunoblot with commercially available anti-phosphotyrosine antibodies.

These assays can be used to discover compounds which block the activation of CSBPβ protein kinase activity and to improve the potency of already discovered compounds. These compounds would be expected to have utility due to their blocking of cytokine synthesis.

The ability of human CSBPβ to rescue a HOG1 deletion strain upon growth in conditions of high osmolarity allows for the direct screening of compounds which block CSBPβ activity in vivo. For example, compounds could be screened for their ability to block growth of a CSBPβ+/HOG1− yeast strain in high osmolarity but which have no effect on growth of the same strain in standard osmolarity or on a CSBPβ−/HOG1+ in high osmolarity. The sensitivity of the yeast based assay can be increased by introducing host mutations that affect the cell membrane and permeability (Gaber, et al., *Mol. Cell. Biol.* 9: 3447–3456. (1989)).

In a compound screening embodiment of this invention, the CSBPβ in isolated, immobilized or cell bound form is contacted with a plurality of candidate molecules and those candidates are selected which bind to and interact with the protein. The binding or interaction can be measured directly by using radioactively labeled candidate of interest or indirectly by measuring an effect resulting from the interaction or binding of the candidate compound. Alternatively, the candidate compounds can be subjected to a competition screening assays, in which a known ligand, preferably labeled with an analytically detectable reagent, most notably radioactivity, is introduced with the compounds to be tested and the compound's capacity to inhibit or enhance the binding of the labeled ligand is measured. Compounds are screened for their increased affinity and selectivity for the CSBPβ.

To illustrate this aspect of the invention, a natural product screen may be performed.

The standard assay in which bound ligand is separated from free by exclusion chromatography using mini-columns is used to initiate a screening effort Marine extracts, microbial extracts and extracts of plant material may be tested for inhibition of a $^3$H-CSAID binding to THP.1 cytosol. Extracts are confirmed as antagonists if binding, is characterized by $IC_{50}$'s of around 80–200 μg/ml. A low hit-rate coupled with the failure to observe inhibition by any of a selected group of "nuisance extracts" indicates that the assay is sufficiently selective and robust to support a screening effort.

Further refinement of the binding assay to facilitate high throughout screening can be achieved by the minor modification of separating bound ligand from free ligand using spin columns.

Inhibitors

The discovery that the CSBPβ of this invention is homologous to the CSBP-MAP kinase family of serine-threonine protein kinases provides a specific rationale for the treatment of a wide variety of acute and chronic inflammatory diseases. Accordingly, it is a further aspect of this invention to treat patients suffering from the effects of cytokine-mediated inflammatory disease with a CSBPβ inhibitory amount of a CSAID. Illustrative examples of such diseases include, without limitation, diseases associated with the central nervous system such as senile dementia of the Alzheimer's type (SDAT), mutiple sclerosis, cerebral malaria, stroke, head trauma and spinal cord injury; cardiovascular diseases such as restenosis and atherosclerosis; inflammatory diseases such as Adult Respiratory Disease Syndrome (ARDS), Rheumatoid arthritis, Osteoarthritis, Inflammatory Bowel Disease (IBD), psoriasis, dermatitis, asthma; and other such diseases or conditions associated with dysregulated or excess cytokines such as osteoporosis, sepsis due to surgical or traumatic incident, chronic renal failure, AIDs, cachexia and autoimmune conditions such as lupus erthyromatosis, host graft rejection and graft verus host disease. Thus this invention contemplates the treatment and/or amelioration of such disease by administering a CSBPβ inhibiting amount of a compound. Without wishing to be bound by any particular theory of the functioning of the CSBPβs of this invention, it is believed that among the useful inhibitors of CSBPβ function are those compounds which inhibit the kinase activity of the CSBPβs. Other sites of inhibition are, of course, possible owing to its position in a signal transduction cascade. Therefore, inhibiting the interaction of CSBPβ with one or more of its upstream or downstream substrates is also contemplated by this invention.

Compositions/Administration

This invention also contemplates pharmaceutical compositions comprising compounds when identified by the above methods and a phanmaceutically acceptable carrier. Pharmaceutical compositions of proteineous drugs of this invention are particularly useful for parenteral administration, i.e., subcutaneously, intramuscularly or intravenously. The compositions for parenteral administration will commonly comprise a solution of the compounds of the invention or a cocktail thereof dissolved in an acceptable carrier, preferably an aqueous carrier. A variety of aqueous carriers may be employed, e.g., water, buffered water, 0.4% saline, 0.3% glycine, and the like. These solutions are sterile and generally free of particulate matter. These solutions may be sterilized by conventional, well known sterilization techniques. The compositions may contain pharmaceutically acceptable auxiliary substances as required to approximate physiological conditions such as pH adjusting and buffering agents, etc. The concentration of the compound of the invention in such pharmaceutical formulation can very widely, i.e., from less than about 0.5%, usually at or at least about 1% to as much as 15 or 20% by weight and will be selected primarily based on fluid volumes, viscosities, etc., according to the particular mode of administration selected.

Thus, a pharmaceutical composition of the invention for intramuscular injection could be prepared to contain 1 mL sterile buffered water, and 50 mg of a compound of the invention. Similarly, a pharmaceutical composition of the invention for intravenous infusion could be made up to contain 250 ml of sterile Ringer's solution, and 150 mg of a compound of the invention. Actual methods for preparing parenterally administrable compositions are well known or will be apparent to those skilled in the art and are described in more detail in, for example, *Remington's Pharmaceutical Science,* 15th ed., Mack Publishing Company, Easton, Pa.

The compounds described herein can be lyophilized for storage and reconstituted in a suitable carrier prior to use. This technique has been shown to be effective with conventional proteins and art-known lyophilization and reconstitution techniques can be employed.

In situations where the identified drug is non-proteineous, it may be administered alone or in combination with pharmaceutically acceptable carriers. The proportion of which is determined by the solubility and chemical nature of the compound, chosen route of administration and standard pharmaceutical practice. For example, they may be administered orally in the form of tablets or capsules containing such excipients as starch, milk sugar, certain types of clay and so forth. They may be administered sublingually in the form of troches or lozenges in which the active ingredient is mixed with sugar and corn syrups, flavoring agents and dyes; and then dehydrated sufficiently to make it suitable for pressing into a solid form. They may be administered orally in the form of solutions which may be injected parenterally, that is, intramuscularly, intravenously or subcutaneously. For parenteral administration, they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. The physician will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as other serotonergic agents and the dosage level is of the same order of magnitude as is generally employed with these other therapeutic agents. The therapeutic dosage will generally be from 1 to 10 milligrams per day and higher although it may be administered in several different dosage units. Tablets containing from 0.5 to 10 mg. of active agent are particularly useful.

Depending on the patient condition, the pharmaceutical composition of the invention can be administered for prophylactic and/or therapeutic treatments. In therapeutic application, compositions are administered to a patient already suffering from a disease in an amount sufficient to cure or at least partially arrest the disease and its complications. In prophylactic applications, compositions containing the present compounds or a cocktail thereof are administered to a patient not already in a disease state to enhance the patient's resistance.

Single or multiple administrations of the pharmaceutical compositions can be carried out with dose levels and pattern being selected by the treating physician. In any event, the pharmaceutical composition of the invention should provide a quantity of the compounds of the invention sufficient to effectively treat the patient.

Probes

The nucleic acid embodiment of this invention is particularly useful in providing probes capable of specific hybridization with human CSBPβ sequences. Probing technology is well known in the art, and it is appreciated that the size of the probes can vary widely, but it is preferred that the probe be at least 15 nucleotides in length. It is also appreciated that such probes can be, and are preferably, labeled with an analytically detectable reagent to facilitate identification of the probe. Useful reagents include, but are not limited to, radioactivity, fluorescent dyes or enzymes capable of catalyzing the formation of a detectable product. This invention contemplates, for example using receptor encoding probes in the diagnostic evaluation of disease states characterized by an abnormal, i.e. increased or decreased level of receptor gene expression. Alternatively, the probes can be used to identify individuals carrying chromosomal or molecular mutations in the gene encoding the receptor. Depending on the conditions employed by the ordinary skilled artisan, the probes can be used to identify and recover additional examples of this receptor (in its genomic or cDNA form) from other cell types and individuals. As a general rule, the more stringent the hybridization conditions, the more closely related the genes will be that are recovered.

Antisense

Also within the scope of this invention are antisense oligonucleotides predicated upon the sequences disclosed herein for the CSBPβ. Synthetic oligonucleotides or related antisense chemical structural analogs are designed to recognize and specifically bind to a target nucleic acid encoding the receptor gene and inhibit gene expression, e.g., the translation of the gene when the target nucleic acid is mRNA. Although not wishing to be bound to a particular theory for the mechanism of action of antisense drugs, it is believed that such drugs can act by one or more of the following mechanisms: by binding to mRNA and inducing degradation by endogenous nucleases such as RNase I or by inhibiting the translation of mRNA by inhibiting its binding to regulatory factors or ribosomal components necessary for productive protein synthesis. Additionally, the antisense sequences can be use as components of a complex macromolecular arrays in which the sequences are combined with ribozyme sequences or reactive chemical groups and are used to specifically target mRNAs of interest and degrade or chemically modify said mRNAs. The general field of antisense technology is illustrated by the following disclosures, which are incorporated herein by reference for purposes of background (Cohen, J. S., *Trends in Pharm. Sci.* 10:435 (1989) and Weintraub, H. M. *Scientific American* January (1990) at page 40).

Gene Therapy

This invention also contemplates the use of the DNA sequences disclosed herein in gene therapy. Because CSBPβ is a protein kinase, it is possible to make a site specific mutant which is inactive as a kinase, but will block activation of the endogenous CSBPβ when coexpressed in the same cell, i.e., it is a dominant negative mutant (Kolch et al., *Nature* 349: 426–428 (1991)). The DNA encoding this mutant protein could be used in gene therapy to reduce chronic inflammation. There are many vector and delivery systems available to direct DNA into target cells in vivo, e.g. adenovirus, retroviruses.

Antibodies

This invention also contemplates antibodies, monoclonal or polyclonal directed to epitopes corresponding to amino acid sequences disclosed herein from the CSBPβ. Particularly important regions of the receptor for immunological purposes are those regions associated with ligand binding domains of the protein. Antibodies directed to the regions are particularly useful in diagnostic and therapeutic applications because of their effect upon protein- ligand interaction. Methods for the production of polyclonal and monoclonal antibodies are well known, see for example Chap. 11 of Ausubel et al. (supra).

This invention also provides pharmaceutical compositions comprising an effective amount of antibody or fragment thereof directed against the CSBPβ to block binding of the naturally occurring ligands to that protein in order to treat or ameliorate disease states associated with protein activation.

The binding proteins of the present invention or their fragments comprising at least one epitope can be used to produce antibodies, both polyclonal and monoclonal. If polyclonal antibodies are desired, a selected mammal, (e.g., mouse, rabbit, goat, horse, etc.) is immunized with a binding protein of the present invention, or its fragment, or a mutated binding protein. Serum from the immunized animal is collected and treated according to known procedures. When serum containing polyclonal antibodies is used, the polyclonal antibodies can be purified by inmuunoaffinity chromatography or other known procedures.

Monoclonal antibodies to the proteins of the present invention, and to the fragments thereof, can also be readily produced by one skilled in the art. The general methodology for making monoclonal antibodies by using hybridoma technology is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies and T-cell Hybridomas" (1981); Kennett et al, "Monoclonal Antibodies" (1980); see also U.S. Pat. Nos. 4,341,761; 4,399,121; 4,427,783; 4,444,887; 4,452,570; 4,466,917; 4,472,500; 4,491,632; and 4,493,890. Panels of monoclonal antibodies produced against the protein of interest, or fragment thereof, can be screened for various properties; i.e., for isotype, epitope, affinity, etc. Alternatively, genes encoding the monoclonals of interest may be isolated from the hybridomas by PCR techniques known in the art and cloned and expressed in the appropriate vectors. Monoclonal antibodies are useful in purification, using immunoaffinity techniques, of the individual proteins against which they are directed. The antibodies of this invention, whether polyclonal or monoclonal have additional utility in that they may be employed reagents in immunoassays, RIA, ELISA, and the like. In addition they can be used to isolate the CSBPβ from human cells and determine the effect of different stimuli and compounds on the phosphorylation state and protein kinase activity of endogenous CSBPβ. The antibodies could be used to establish a tissue culture based assay for discovery or modification of novel compounds which block the phosphorylation or kinase activity of CSBPβ. An example of such an assay would be to incubate human cell lines expressing CSBPβ with a compound or compound mixture prior to treatment with a suitable LPS stimulus (e.g., LPS, osmotic stress)for a defined time period, followed by immunoprecipitation of CSBPβ with antibody and assessment of its phosphorylation state via immunoblot or chromatography or measurement of its kinase activity with appropriate protein or peptide substrate.

Transgenics

Transgenic, non-human, animals may be obtained by transfecting appropriate fertilized eggs or embryos of a host with nucleic acids encoding the CSBPβ disclosed herein, see for example U.S. Pat. Nos. 4,736,866; 5,175,385; 5,175,384 and 5,175,386. The resultant transgenic animal may be used as a model for the study of CSBPβ/ligand interaction. Particularly, useful transgenic animals are those which display a detectable phenotype associated with the expression of the protein. Drugs may then be screened for their ability to reverse or exacerbate the relevant phenotype. This invention also contemplates operatively linking the CSBPβ coding gene to regulatory elements which are differentially responsive to various temperature or metabolic conditions, thereby effectively turning on or off the phenotypic expression in response to those conditions.

The nucleic acid probes disclosed herein can be used to clone the cognate version of the human CSBPβ gene from a desired experimental animal species; for example the murine version. Strains of mice can be developed in which said gene has been eliminated by conventional gene knockout technology. The gene can then be substituted/or replaced by the human CSBPβ DNA of this invention to yield a mouse for screening candidate drugs in vivo. Similar gene knockout and human protein inhibition studies can also be performed with yeast

EXAMPLES

The present invention is further described by the following examples. The examples are provided solely to illustrate the invention by reference to specific embodiments. These exemplification's, while illustrating certain specific aspects of the invention, do not portray the limitations or circumscribe the scope of the disclosed invention.

Certain terms used herein are explained in the foregoing glossary.

All examples are carried out using standard techniques, which are well known and routine to those of skill in the art, except where otherwise described in detail. Routine molecular biology techniques of the following examples can be carried out as described in standard laboratory manuals, such as Sambrook et aL

Example 1

Tissue Distribution

A Northern blot was conducted with a partial CSBPβ cDNA above on a human multiple tissue Northern from Clontech. Conditions used have been reported previously (Lee, J. C., Laydon, J. T., McDonnell, P. C., Gallagher, T. F., Kumar, S., Green, D., McNulty, D., Blumenthal, M. J., Heys, J. R., Landvatter, S. W., Strickler, J. E., McLaughlin, M. M., Siemens, I. R., Fisher, S. M., Livi, G. P., White, J. R., Adams, J. L., and Young, P. R. (1994) *Nature* 372, 739–746). CSBPβ was expressed most abundantly in human testis, with lower expression in pancreas, prostate and small intestine. Weak expression was noted in spleen, thymus, PBL, and skeletal muscle.

Example 2

Homologo to MAP Kinase Family and Expression

CSBPβ is a member of the MAP kinase family of serine-threonine protein kinases (Marshall, C. J. (1994) *Curr. Opinion Genet. Develop.* 4, 82–89). Members of the MAP kinase family are characterized by having a "T×Y" amino acid motif (T=Threonine, Y=tyrosine and X is any amino acid) in an activation loop near to the active site. Phosphorylation of both the tyrosine and threonine by a MAP kinase kinase in response to an appropriate stimulus is required for the activation of MAP kinase activity. There are three families of MAP kinases which are distinguished by the nature of the "x" amino acid and the size of the activation loop (Cano, E., and Mahadevan, L. C. (1995) *Trends Biochem Sci.* 20, 117–122). Hence, the erks have TEY, JNK/SAPKs have TPY and the CSBP/p38s have TGY. These differences reflect differences in the activating MAP kinase kinases and in the cellular stimuli which activate each MAP kinase. Within each family, the activating stimuli appear to be very similar. Thus the erks respond mostly to mitogenic stimuli (e.g., EGF, PDGF), while the JNK/SAPKs and CSBP/p38s respond to several cellular stresses (eg UV, osmotic, heat or chemical stress, hypoxia, oxidants etc) and proinflammatory stimuli (e.g., LPS, IL-1, TNF, etc.).

Recently, several new forms of CSBP have been identified. In addition to the two splice variants of CSBP, CSBP1 and CSBP2, a further spliced variant was identified through a yeast two-hybrid interaction screen with the nuclear protein Max ( Zervos, A. S., Faccio, L., Gatto, J. P., Kyriakis, J. M., and Brent, R. (1995) *Proc. Natl. Acad. Sci. USA* 92, 10531–10534). Two homologues with significant amino acid identity which also retain the "TGY" motif characteristic of the CSBP family were also recently identified: p38β(Jiang, Y., Chen, C., Li, Z., Guo, W., Gegner, J. A., Lin, S., and Han, J. (1996) *J. Biol. Chem.* 271, 17920–17926), and ERK6/SAPK3 (Lechner, C., Zahalka, M. A., Giot, J.-F., Moller, N. P. H., and Ullrich, A. (1996) *Proc. Natl. Acad. Sci. USA* 93, 4355–4359; Mertens, S., Craxton, M., and Goedert, M. (1996) *FEBS Lett.,* (In press).

CSBPβ may be engineered for yeast expression in a similar manner to that previously described for CSBP1 and CSBP2 (Kumar, S., McLaughlin, M. M., McDonnell, P. C., Lee, J. C., Livi, G. P., and Young, P. R. (1995) *J. Biol. Chem.* 270, 29043–29046). An XhoI site is engineered at the initiation codon of CSBPβ by the polymerase chain reaction (Mullis and Faloona, Meth. Enymol. 155:335–50 (1987). An XhoI/BglII fragment containing CSBPβ is then ligated into the same sites in p138NBU, a modification of p138NB (McHale et al. Mol. Pharm. 39:109–113 (1991)) in which the Trp selectable marker is replaced with URA3. Alternatively, the amino terminus of CSBPβ can be fused to an epitope tag such as the FLAG epitope (for which reagents are available from IBI-Kodak) by using a polymerase chain reaction which includes an XhoI site, the FLAG epitope and the amino terminal nucleotide sequence of CSBPβ.

CSBPβ can also be engineered for expression in mammalian cells such as HeLa and JURKAT by fusing the amino terminus of CSBPβ with a FLAG epitope. An XbaI/XhoI restriction fragment containing the complete open reading frame of human CSBPβ was excised from the Bluescript plasmid in which it was originally cloned, and inserted into the vector pSPORT (GIBCO-BRL) cut with XbaI and SalI. The resulting vector pSPORT-CSBPβ was then cut with SacI and BamHI and ligated with a synthetic oligonucleotide linker prepared by hybridizing together the following two oligonucleotides: 5' GAT CCG GTA CCA TGG ATT ATA AAG ATG ATG ATG ATA AAA GCC TCA TCC GGA AAA AGG GCT TCT ACA AGC AGG AGC T - 3' (SEQ ID NO: 3) and 5'-CCT GCT TGT AGA AGC CCT TTT TCC GGA TGA GGC TTT TAT CAT CAT CAT CTT TAT AAT CCA TGG TAC CG - 3' (SEQ ID NO: 4) to create pSPORT-FLAGCSBPb. The entire FLAG- CSBPβ fusion was then excised from pSPORT-FLAG CSBPβ on a HindIII/SmaI restriction fragment, and ligated into pCDN cut with HindIII and EcoRV to create pCDN-FLAGCSBPb. This could then be transfected into mammalian cells such as HeLa or JURKAT using a number of established protocols, eg lipofectamine (GIBCO-BRL). Treatment of cells with a suitable stimulus (eg osmotic shock, UV, IL-1) leads to activation of the FLAG-CSBPb, and CSAID binding can be detected through the ability of CSAIDs to inhibit the kinase activity of CSBPb. Thus, FLAG CSBPβ can be immunoprecipitated from transfected mammalian cells with antibodies to the FLAG epitope (IBI-Kodak), and an in vitro kinase assay can be performed with a suitable substrate (eg myelin basic protein, MAPKAP kinase-2 or –3) in the presence or absence of CSAID as previously described (Lee et al., (1994) *Nature* 372:739–746; McLaughlin et al. *J. Biol. Chem.* 271:8488–8492 (1996)).

Example 3

Expression in *E. coli*

To confirm that the proteins encoded by the isolated cDNAs of this invention can bind to CSAIDs, the cDNA may be expressed in *E. coli,* yeast and mammalian cells (e.g., HeLa, CHO, 3T3). In *E. coli* the CSBPs are expressed as fusion proteins, for example, with β-galactosidase, an enterokinase cleavable FLAG epitope tag, glutathione S-transferase or a hexaHistidine tail. (FLAG is a commercial epitope for which reagents are available through IBI-Kodak). In the latter case this is achieved by the design of a synthetic oligonucleotide linker with an initiation site, antibody recognition sequence, and enterokinase cleavage site. Proteins are expressed under the control of either the pLac (e.g., Bluescript KS vector from Stratagene, LaJolla, Calif.) or λpL (Shatzman, et al., N.Y. Acad. Sci., 478: 233–248 (1986)) promoters and probed with a radiophotoaffinity CSAIDs shown to specifically crosslink proteins of the expected sizes in cell lysates.

Protein expressed in *E. coli* is purified by passage over an affinity matrix containing a monoclonal antibody to the FLAG epitope, glutathione beads or a NiNTA column according to manufacturer's instructions.

What is claimed is:

1. An isolated polynucleotide encoding a polypeptide comprising the amino acid sequence as set forth in SEQ ID NO:2.

2. The polynucleotide of claim 1 wherein the polynucleotide is DNA.

3. The polynucleotide of claim 1 wherein the polynucleotide is RNA.

4. The polynucleotide of claim 1 comprising the nucleotide sequence as set forth in SEQ ID NO: 1.

5. The polynucleotide of claim 1 comprising nucleic acid residues 1–1838 as set forth in SEQ ID NO: 1.

6. An expression vector comprising the polynucleotide of claim 1.

7. A host cell comprising the vector of claim 6.

8. A process for producing a polypeptide comprising expressing from the host cell of claim 7 a polypeptide encoded by said polynucleotide.

9. A process for producing a cell which expresses a polypeptide comprising transforming or transfecting the cell with the vector of claim 6 such that the cell expresses the polypeptide encoded by the polynucleotide contained in the vector.

10. An isolated polynucleotide which is complementary to a polynucleotide sequence encoding the amino acid sequence of SEQ ID NO:2.

11. The polynucleotide of claim 10 which is complementary to the nucleotide sequence of SEQ ID NO: 1.

* * * * *